United States Patent [19]

Edelman et al.

[11] Patent Number: 4,878,646

[45] Date of Patent: Nov. 7, 1989

[54] PINCH VALVE MECHANISM FOR A PARENTERAL INFUSION SYSTEM

[75] Inventors: Howard Edelman, San Francisco; Carl Ritson, San Jose, both of Calif.

[73] Assignee: Critkon, Inc., Tampa, Fla.

[21] Appl. No.: 231,920

[22] Filed: Aug. 15, 1988

[51] Int. Cl.⁴ ............................................. F16L 55/14
[52] U.S. Cl. ............................................ 251/9; 251/66; 251/68; 604/250
[58] Field of Search .................... 251/66, 68, 9, 11; 604/66, 250

[56] References Cited

U.S. PATENT DOCUMENTS

| | | | |
|---|---|---|---|
| 2,181,523 | 11/1939 | Shiels | 251/68 |
| 3,991,972 | 11/1976 | Eaton | 251/11 |
| 4,637,817 | 1/1987 | Archibald et al. | 251/68 |
| 4,645,489 | 2/1987 | Krumme et al. | 251/11 |
| 4,673,389 | 6/1987 | Archibald et al. | 251/9 |

Primary Examiner—A. Michael Chambers
Attorney, Agent, or Firm—W. Brinton Yorks, Jr.

[57] ABSTRACT

A pinch valve mechanism for a parenteral infusion system is provided which includes a spring-loaded pinch valve. The pinch valve is manually latched to its open position. A bobbin and cam mechanism includes a length of wire which contracts when a current is applied to it. The cam has two positions, one which holds the pinch valve in its open position and one which enables to pinch valve to close. When it is desired to automatically close the pinch valve, a current is applied to the wire. The contraction of the wire moves the cam from its valve open position to its alternate position, permitting the pinch valve to spring closed.

11 Claims, 7 Drawing Sheets

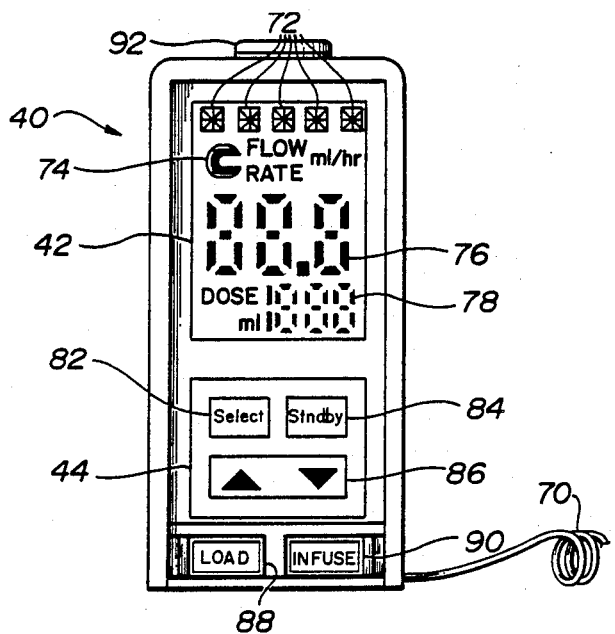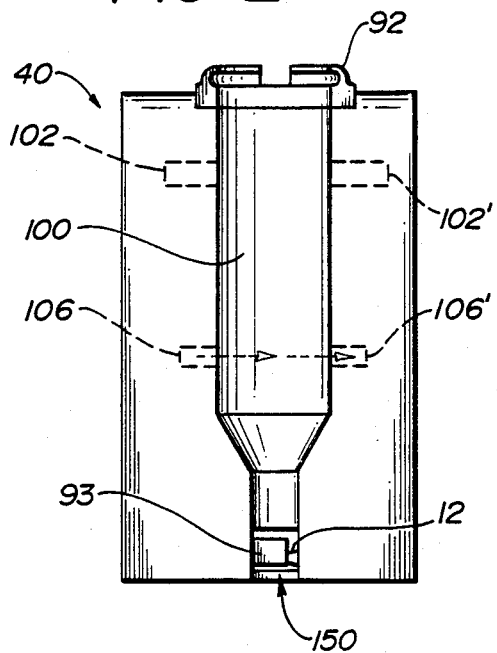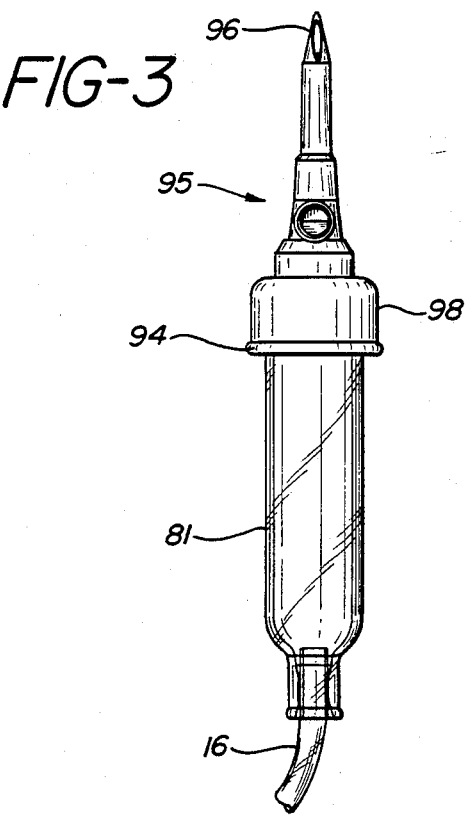

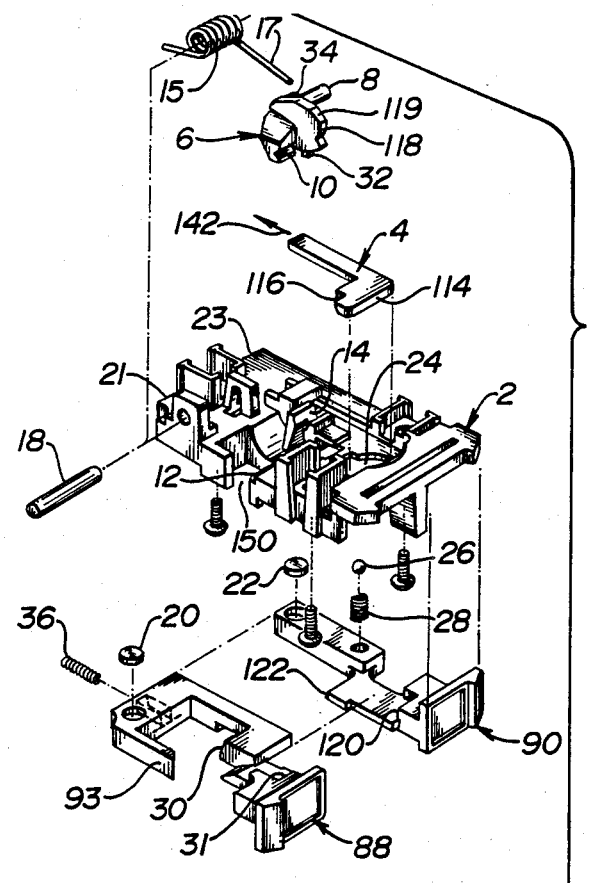
FIG-4
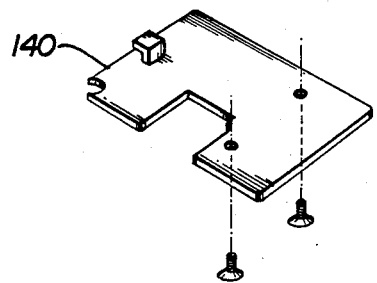
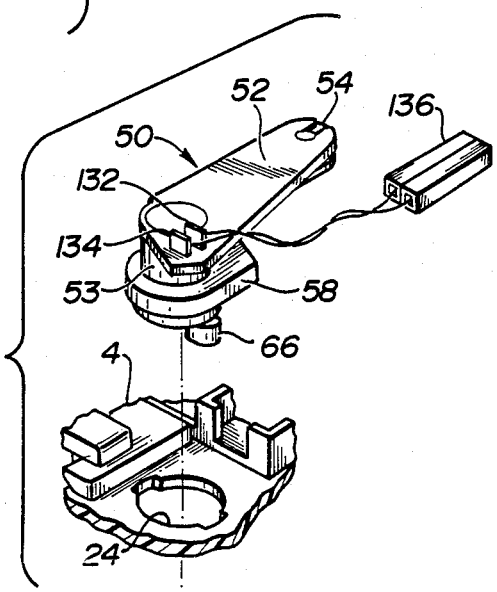
FIG-5

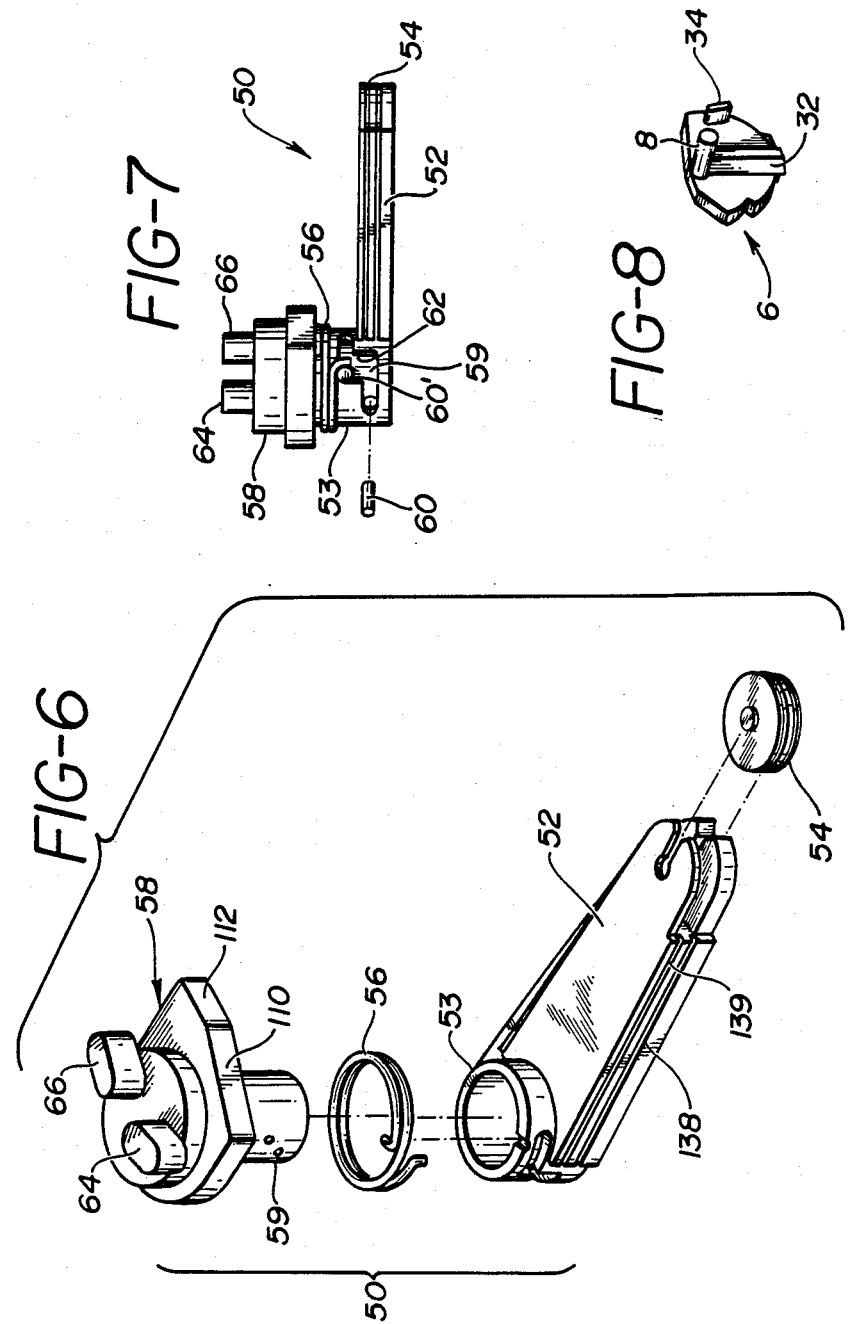

PINCH VALVE MECHANISM FOR A PARENTERAL INFUSION SYSTEM

This invention relates to systems for the delivery of parenteral solutions and, in particular, to a pinch valve for controllably occluding a tubing section in such systems.

In parenteral infusion systems which deliver parenteral solutions to a patient, it is frequently necessary to controllably occlude and open tubing sections in a fluid administration set for the controlled delivery of solutions to the patient. Manually operated tube clamps are known in the art; however an automated fluid delivery system must utilize clamps or valves which can be actuated automatically under control of a fluid delivery controller. A conventional technique for implementing an automatically controlled valve is to open and close a pinching mechanism with a solenoid. A sufficiently sized solenoid can provide the substantial pinching force of 1.5 pounds or greater necessary to completely occlude the flow of solution through medical tubing when actuated.

A solenoid providing the necessary closing force will generally be of a significant size, and will occupy a substantial space in the enclosure of the infusion device. It is desirable for components in a parenteral infusion device to be a small as possible, since ease of portability is an important requirement for a parenteral infusion system in a hospital. Furthermore, a large solenoid will require a substantial amount of power when activated. This presents an acute problem in the design of infusion devices, particularly when the device is to be battery operated. The current drain of repeated actuations of a solenoid can quickly consume the available operating current in a battery-powered infusion device. Accordingly it is desirable for an automatically actuated pinch valve in a parenteral infusion system to be as small as possible, and to require as little power as possible when actuated.

In accordance with the principles of the present invention, a controllably actuated pinch valve mechanism is provided for a parenteral infusion system. The mechanical portion of the mechanism includes a spring-loaded pinch valve which is manually opened and latched, thereby permitting solution to flow through a tube passing through the pinch valve. As the Pinch valve is latched open, a cammed surface is rotated into a position which maintains the pinch valve in its open position. The cammed surface is attached to a bobbin arrangement which is wound with a wire that will contract when heated by a current passing through it. When it is desired to close the pinch valve so that the tubing in the mechanism will be occluded, a current is applied to the wire, causing the wire to contract and rotate the cammed surface. The cammed surface rotates to a position that releases the pinch valve, and the pinch valve will spring shut, occluding the tubing.

It has been found that the wire used in the bobbin arrangement requires only a very small current to contract as necessary for actuation of the pinch valve. In a preferred embodiment, the wire is pulsed with a square wave, with the duty cycle of the square wave affording economy in current consumption over a direct current actuated device. The bobbin arrangement is wound with several turns of wire to increase the force utilized to rotate the cammed surface. The bobbin arrangement is substantially smaller than a solenoid of equivalent capability, occupying only a small space in a parenteral infusion device.

In the drawings:

FIGS. 1, 2, and 3 illustrate a parenteral infusion device constructed in accordance with the present invention;

FIGS. 4 and 5 are exploded views of a pinch valve mechanism suitable for use in the device of FIGS. 1 and 2 and constructed in accordance with the principles of the present invention;

FIGS. 6, 7, 9, and 10 illustrate the bobbin assembly of the mechanism of FIGS. 4 and 5;

FIG. 8 is a perspective view of the shut-off arm of the mechanism of FIGS. 4 and 5;

Figure 13:
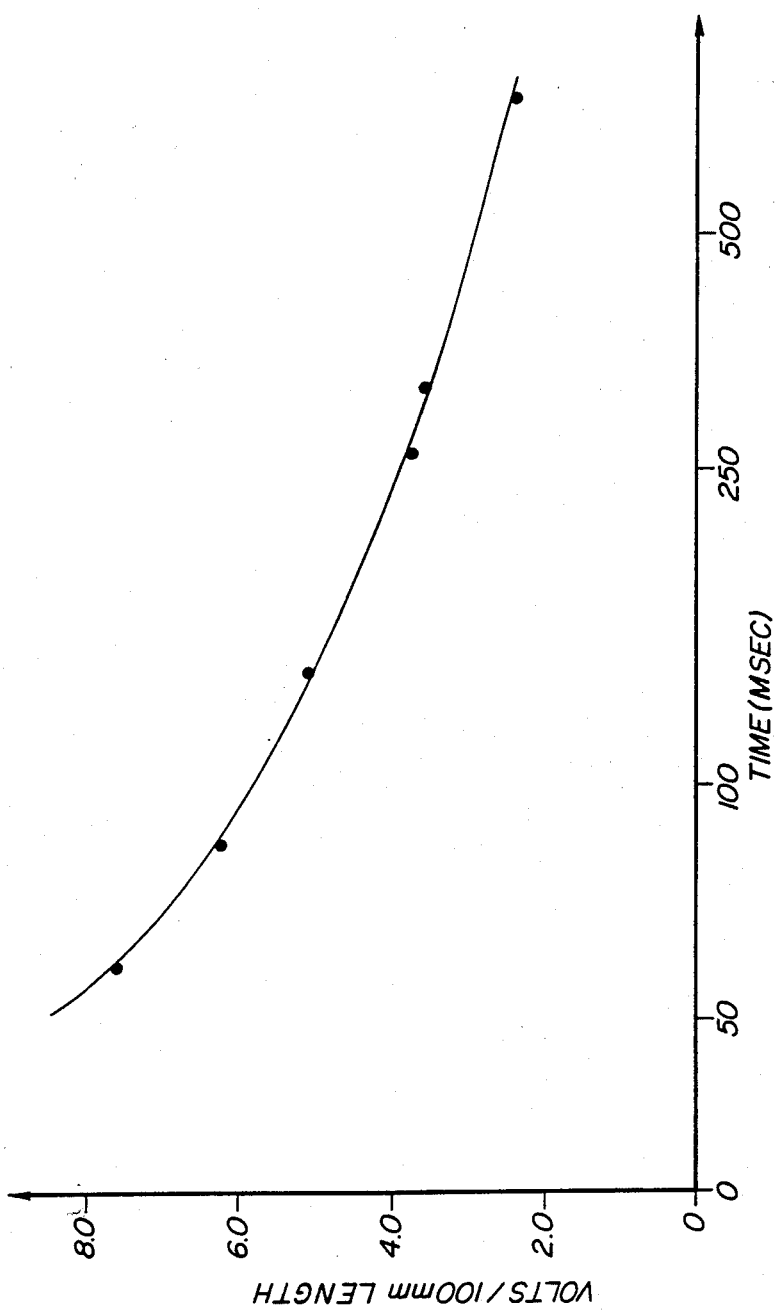
Figure 14:
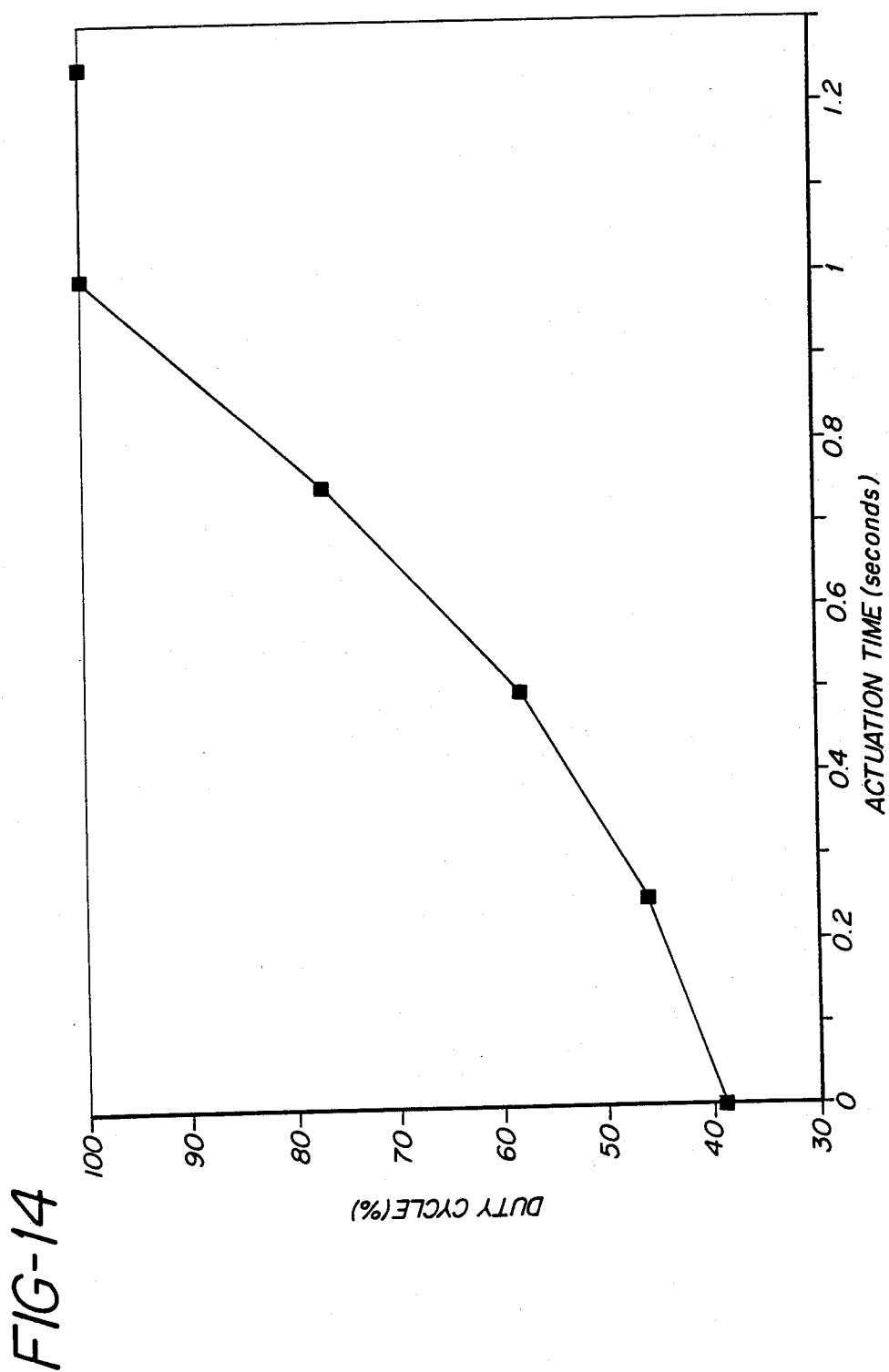

FIG. 13 graphically illustrates the actuation time of the pinch valve mechanism of FIGS. 4 and 5 as a function of applied voltage; and FIG. 14 graphically illustrates the preferred pulse modulation drive sequence used to actuate the pinch valve mechanism of the present invention.

Referring first to FIGS. 1-3, a parenteral infusion device constructed in accordance with the principles of the present invention is shown in front and side views, along with a drip chamber 81 about which the device mounts. The particular device shown is a secondary infusion monitor, which is more fully described in the context of a dual source parenteral infusion system in concurrently filed U.S. patent application Ser. No. 07/232,058, filed 08/15/88, entitled DUAL SOURCE PARENTERAL INFUSION SYSTEM WITH SECONDARY INFUSION MONITOR.

On the front of the monitor 40 as shown in FIG. 1 is a display 42. A five character message center 72 is located at the top of the display. These fourteen segment characters display alarm and status conditions during the administration of a parenteral solution. Below the message center is an instrument logo design 74 which pulses during delivery of the parenteral solution. Below the logo are three large characters 76 which display the flow rate of the solution. The notation "FLOW RATE" and the flow units of ml/hr are displayed above the flow rate numerals. Below the flow rate are three and one-half characters 78 which display the dose being administered, together with the notation "DOSE" and the units of ml.

Below the display 42 are a series of pushbuttons 44, which are used to program and operate the monitor 40. The "SELECT" pushbutton 82 is depressed to program the monitor. When this pushbutton is depressed, the value being entered flashes on the display, and the value is incremented or decremented by depressing the up-/down pushbutton 86. The "STANDBY" pushbutton 84 is depressed to stop the administration of the parenteral solution, or to clear the alarms on the monitor. Below the pushbutton 86 is a "Load" key 88, which is depressed while mounting the secondary infusion monitor around the drip chamber 81. An "Infuse" key 90 is depressed to begin the administration of the parenteral solution.

A side view of the secondary infusion monitor is shown in FIG. 2. A cavity 100 in the monitor is accessible from the side for insertion of the drip chamber 81 shown in FIG. 3. At the top of the monitor is a mounting ring 92. The secondary infusion monitor is mounted around the drip chamber 81 by inserting the lip 94 of the drip chamber spike 95 into the mounting ring 92. An integrally molded drop former is located inside the cap 98 of the spike 95. When so engaged in the monitor cavity, the drip chamber 81 is positioned in the optical path of a drop detector 102, 102', and in the optical path of a low level detector 106, 106'. To properly engage the drip chamber in the cavity 100 a barrier 93 must be withdrawn from the bottom of the cavity 100. The barrier is withdrawn by depressing the "Load" key, whereupon the tubing section 16 is located in the passage at the bottom 150 of the cavity. When the "Load" key is released the barrier 93 encloses the tubing section 16 in the bottom 150 of the cavity and the tubing section 16 is pinched closed by a pinch valve inside the cavity. Fluid flow is thereby prevented until the "Infuse" key is depressed at the commencement of fluid delivery.

The interacting components of the pinch valve mechanism of the present invention, located above the Load and Infuse keys and including those keys, are shown in the exploded view of FIG. 4. The components of the pinch valve mechanism are mounted on a molded chassis 2. The molded components shown in the drawings are preferably made of a glass filled nylon material to present a smooth finish. Slideably mounted between the underside of the chassis and a base plate 140 are the Load key 88 and the Infuse key 90. Integrally formed as a part of the Load key is the forward extending barrier 93. A Load key return spring 36 mounts in a slot in the back of the Load key, with the rearward end of the spring 36 abutting against the rear wall of the chassis. A magnet 20 is located in a hole in the rear of the Load key. A magnetic reed switch is mounted on a printed circuit board located above the chassis as indicated at 21. As the Load key is depressed rearward, this magnet will move beneath and close the reed switch. The closure of the reed switch provides a signal to the processor in the monitor, informing the processor that the Load key has been depressed.

The Infuse key 90 similarly has a magnet 22 located in the rear for detection of activation of the Infuse key. When depressed the magnet 22 will move beneath a position 23 on the chassis where a second magnetic reed switch is mounted on a printed circuit board. A detent spring 28 and detent ball 26 are located in a hole in the upper surface of the Infuse key. The detent ball will become positioned in either of two depressions on the underside of the chassis as the Infuse key is depressed and released, thereby lightly holding the Infuse key in either of these positions giving the user the tactile sensation that the Infuse key is properly positioned.

An L-shaped latch 4 is slideably mounted on the top of the chassis. The latch 4 can slide forward and to the rear. The latch has a front face 114 which opposes cammed surfaces of an inner drum 58 of a bobbin mechanism 50, and a rear face 116 which opposes lower and upper faces 118 and 119 of a shut-off arm 6.

The shut-off arm 6 is pivotally mounted by its integral pivot rod 8 in a seat 14 of the chassis. A pinch face 10 on the left side of the shut-off arm is then located in the cavity 150 of the chassis so that the pinch face opposes a Pinch blade 12 formed in the chassis at the front of the cavity 150. The pinch blade and face angularly engage so as to completely occlude tubing 16 without deforming the tubing. The pinch face is forceably urged against the blade by a shut-off arm spring 15, which has a forward arm 17 that presses downward against a spring tab 34 on the right side of the shut-off arm (see FIG. 8.) The spring 15 is mounted on the chassis around a spring pin 18 that is located between two apertured projections from the chassis. The shut-off arm 6 also has a shoulder 32 extending downward from the shut-off arm pivot rod 8 on the right side of the arm. Both the Load key 88 and the Infuse key 90 have molded features, described below, which act on the shut-off arm shoulder 32 in order to rotate the shut-off arm about its pivot rod 8 to separate the shut-off arm pinch face 10 and chassis pinch blade 12.

A bobbin mechanism 50 is mounted in an aperture 24 of the chassis, as shown in enlargement in FIG. 5. The bobbin mechanism includes an outer drum 52, an inner drum 58, and an electrical connector 136 wired to two swage pins 132, 134 on the outer drum. The assembly of these and other bobbin components are illustrated in FIGS. 6, 7, 9, and 10.

FIG. 6 shows the assembly of the inner and outer drums of the bobbin mechanism 50. The outer drum 52 has a hub 53 at one end, a slot at the other end, and two parallel grooves 138 and 139 on both sides. A Pulley 54 is rotatably mounted in the slot at the end of the outer drum. A bobbin torsion spring 56 is mounted about the hub 53 with the inward protruding end of the spring 56 engaged in a groove on the hub 53. A shaft 59 of the inner drum 58 is positioned in the hub 53 so that the inner drum will turn within the hub. On the top of the inner drum are a pair of outwardly extending tabs that retain the inner drum in the aperture 24 of the chassis. The inner drum 58 includes a cam face 110 for closing the pinching mechanism and a cam face 112 for opening the pinching mechanism.

With the inner and outer drums and the torsion spring assembled as shown in FIG. 7, two posts 60 and 60' are inserted through a guide slot 62 in the outer drum. The posts 60 and 60' are affixed within holes in the shaft 59 of the inner drum 58. As can be seen in FIG. 7, the upper post 60' is used to hook the downward extending end of the torsion spring 56.

Figure 10:
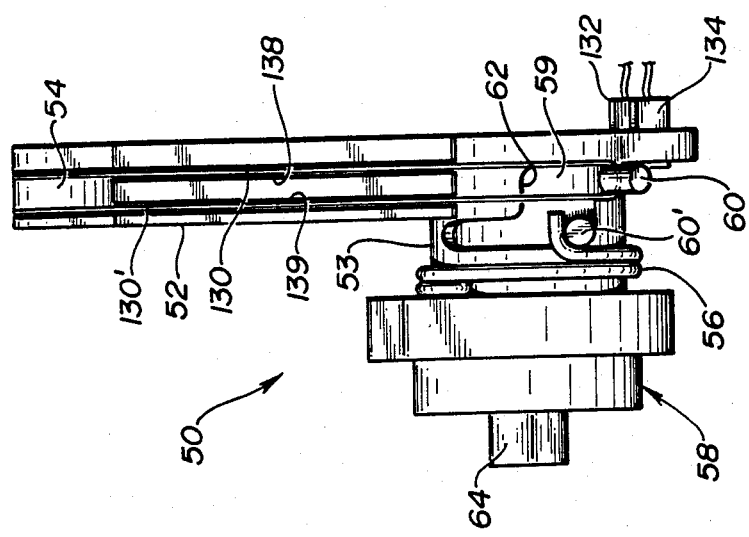
Figure 9:
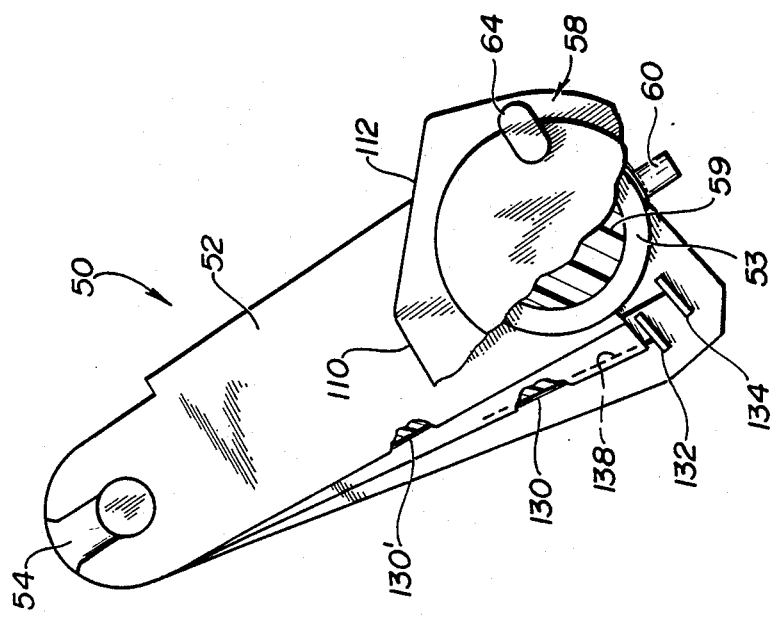

Completion of the assembly of the bobbin mechanism 50 is explained with reference to FIGS. 9 and 10. Two swage pins 132 and 134 are inserted through the outer drum 52. One end of a 4.75 inch length of 6 mil titanium/nickel alloy wire, available from Toki America Technologies, Inc. of Irvine, Calif. is attached to swage pin 132. The wire is then wrapped around the outer drum as indicated at 130 where it is located in the lower groove 138 of the drum and passes around the pulley 54 at the end of the drum. At the other side of the outer drum 52 the wire is looped around the post 60 and wrapped back around the drum. On its return passage the wire is located in the upper groove 139 of the drum and again passes around the Pulley 54, as indicated at 130'. The remaining end of the wire is attached to the other swage pin 134. The loop of wire is kept under tension by the torsion spring 56, since one end of the spring is inserted in the hub 53 of the outer drum (to which the swage pins are attached) and the other end of the spring is hooked to the post 60 in the inner drum shaft 59 (in which the looping post 60 is affixed.) The fully assembled bobbin mechanism 50 is then inserted in the aperture 24 in the chassis 2 as shown in FIG. 5.

Operation of the assembled pinch valve mechanism of the present invention is as follows. Initially the Load and Infuse keys are flush with the face of the monitor. The barrier 93 is extended across cavity 150, and the pinch valve, including the pinch face 10 and the pinch blade 12, is closed. When it is desired to mount the monitor 40 about the drip chamber 81 the Load key 88 is depressed. When the Load key is depressed to the rear, the integral barrier 93 of the Load key is withdrawn from the cavity 150, exposing the pinch valve. A shoulder 30 of the Load key contacts the shoulder 32 of the shut-off arm 6 and pivots the pinch face 10 of the arm away from the pinch blade 12, thereby opening the pinch valve. Simultaneously, a shoulder 31 of the Load key contacts the tab 64 on the inner drum 58 of the bobbin mechanism. This contact will rotate the inner drum 58 in the aperture 24 to a position where the cam face 110 of the drum opposes the front latch face 114 of the latch 4. While the Load key is held depressed to keep the pinch valve open, the tubing 16 is inserted between the pinch face 10 and the pinch blade 12. The lip 94 of the drip chamber cap is snapped into the mounting ring 92 and the Load key is released.

When the Load key is released the force of the spring 15 (nominally about 5.0 pounds) rotates the shut-off arm 6 to close the pinch valve. As the shut-off arm pivots the shoulder 32 of the arm pushes against the Load key shoulder 30 to return the Load key to its undepressed position. The return of the Load key draws the barrier 93 back across the cavity 150. Closure of the pinch valve at this time is enabled because the latch 4 is permitted to slide to its forwardmost, unlatched position against the cam face 110 of the inner drum 58. The shut-off arm 6 can pivot freely, unrestrained by the latch 4.

Figure 11:
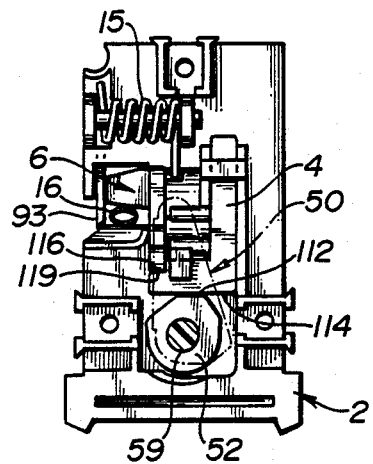
FIGS. 11 and 12 illustrate the pinch valve mechanism of FIGS. 4 and 5 during two states of operation.

When the user is ready to commence fluid delivery the Infuse key 90 is depressed. A shoulder 122 on the Infuse key contacts the shut-off arm shoulder 32 and rotates the pinch face 10 of the valve to open the valve. At the same time a shoulder 120 on the Infuse key contacts the tab 66 on the inner drum 58, rotating the bobbin mechanism back to a position where the cam face 112 of the inner drum opposes the front face 114 of the latch 4. The latch 4 freely moves rearward as indicated by arrow 142 as the cam contacts it because the shut-off arm has rotated to a position where its upper face 119 opposes the rear face 116 of the latch. As the Infuse key is released the valve is held open by the interaction of the cam face 112 pressing against the latch face 114 and the latch face 116 pressing against the upper face 119 of the shut-off arm 6. This orientation is illustrated in the top view of the pinch valve mechanism of FIG. 11. The Infuse key is held in the depressed position by the detent ball 26, and the open valve condition is detected by the reed switch above magnet 22 of the Infuse key. The 5.0 lbs. of force of the shut-off arm spring 15 is thus stored within the mechanism.

Figure 12:
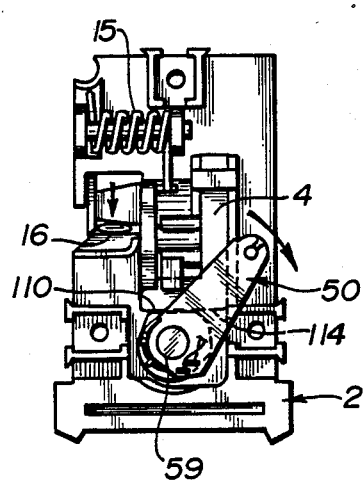

When the delivery of solution has ended and the monitor is automatically close the pinch valve, a small current is applied through the electrical connector 136 to the titanium/nickel wire. This current causes the wire to heat, and as it does so it begins to contract in length. The effective length of the looped wire is only 2.375 inches, but the two runs of wire effectively double the energy imparted by the contracting wire. As the wire contracts, it pulls on post 60, which begins to move in the guide slot 62, rotating the outer drum counterclockwise in relation to the inner drum. The outer drum rotates approximately 7° until it stops against the inside surface of the cavity 100. The inner drum is then rotated clockwise with a force of approximately 5.0 lbs., which is fully sufficient to rotate the inner drum approximately 24°, sliding cam face 112 off of the latch face 114 so that cam face 110 opposes the latch. The latch 4 then snaps forward against the cam face 110, releasing the force against upper face 119 of the shut-off arm 6. The shut-off arm 6 is then free to pivot in response to the released force of spring 15 to close the valve. At this time the inner drum, latch and shut-off arm are oriented as shown in FIG. 12. The rotation of the shut-off arm to the valve closed condition causes the shut-off arm shoulder 32 to press against the shoulder 122 of the Infuse key, thereby returning the Infuse key to its undepressed position.

In a constructed embodiment of the present invention, the titanium/nickel wire length will contract approximately 3%. The actuation time of the pinch valve mechanism is a function of the applied voltage and the length of the wire. In the constructed embodiment the wire length was 121 mm, and the applied voltage used ranged between 4.2 and 9.0 volts. The mechanism was thereby operated in the range between the two dots shown on the actuation curve of FIG. 13.

It has been discovered by the present inventor that the use of a DC current to activate the titanium/nickel wire causes the development of hot spots along the wire and consequential weakening of the wire at these points with prolonged cycling of the pinch valve. This results in a reduced lifetime for the valve. Accordingly, it is preferred to apply current to the wire using a pulse width modulation scheme, with the applied energy being controlled by varying the duty cycle of the pulses. The pulse width modulation scheme has been found to result in more even heating of the wire and the reduction of hot spot occurrences. FIG. 14 illustrates the preferred pulse width modulation scheme, with the duty cycle breakpoints being indicated at the blocks on the graph. The duty cycle starts at approximately 40% and its rate of increase is incremented every 0.25 seconds. At the one second mark a 100% duty cycle is achieved, a DC condition. If the pinch valve has not opened 0.25 seconds after application of the 100% duty cycle current, as deteced by the reed switch above the Infuse key, the pulse width modulator shuts down and the monitor declares a fault condition and alarms. It has been found that the nominal actuation time for the pinch valve of the present invention is less than 0.5 seconds.

By comparison, the solenoid in a conventional pinch valve mechanism may actuate in 50 milliseconds, may weigh approximately 80 grams and require 9 watts to actuate. In addition, a solenoid generates its greatest force at the end of its range of travel. The thermal wire actuator of the present invention will actuate in 70 to 100 milliseconds when heated to 142° C. weighs approximately 1 gram, and requires 2-3 watts to actuate. The force applied by the contracting wire is constant during actuation, and the mechanism of the present invention occupies significantly less space than the typical solenoid.

What is claimed is:

1. A pinch valve mechanism for a parenteral infusion system comprising:
   a spring-loaded pinch valve;
   means for latching said pinch valve to an open condition, whereby the energy of said spring of said pinch valve is stored;
   means, connected to said latching means, for unlatching said pinch valve and releasing said energy of said spring, including a length of wire which contracts upon application of a current; and
   means for applying a current to said wire,
   whereby the application of current to said wire by said current applying means causes said wire to contract and unlatch said pinch valve.

2. The pinch valve mechanism of claim 1, wherein said unlatching means includes a cam oriented in a first position when said pinch valve is latched and oriented in a second position when said pinch valve is unlatched.

3. The pinch valve mechanism of claim 2, wherein said current applying means applies a pulsatile current to said wire.

4. The pinch valve mechanism of claim 3, wherein said pulsatile current exhibits a variable duty cycle.

5. The pinch valve mechanism of claim 1, further including means for opening said pinch valve without latching said valve in its open condition, and means for opening and latching said pinch valve.

6. The pinch valve mechanism of claim 5, further including a moveable barrier for retaining tubing within said pinch valve.

7. The pinch valve mechanism of claim 6, wherein said moveable barrier retracts to permit entry of said tubing into said pinch valve upon actuation of said valve opening means.

8. The pinch valve mechanism of claim 1, wherein said unlatching means further comprises a bobbin mechanism for retaining under tension a length of said wire.

9. The pinch valve mechanism of claim 8, wherein said unlatching means further comprises a cam, connected to said bobbin mechanism, and actuated by said bobbin mechanism to be oriented in a valve open position or a valve closed position, wherein said cam operates to open and close said pinch valve.

10. The pinch valve mechanism of claim 9, wherein said latching means further comprises a latch located between said cam and said pinch valve.

11. The pinch valve mechanism of claim 10, wherein said wire is a titanium/nickel alloy wire.

* * * * *